United States Patent [19]
Bernstein et al.

[11] Patent Number: 5,840,762
[45] Date of Patent: Nov. 24, 1998

[54] METHOD FOR THE TREATMENT OF CARDIAC ARRHYTHMIAS AND SHORTENING OF ACTION POTENTIAL DURATION

[75] Inventors: Joel E. Bernstein, Deerfield; Kenneth M. Verburg, Wheaton, both of Ill.

[73] Assignee: GenDerm Corporation

[21] Appl. No.: 585,872

[22] Filed: Jan. 12, 1996

[51] Int. Cl.$^6$ .................................................. A61K 31/16
[52] U.S. Cl. ............................................................ 514/627
[58] Field of Search ............................................. 514/627

[56] References Cited

U.S. PATENT DOCUMENTS 5,063,060   11/1991   Bernstein .

OTHER PUBLICATIONS

Samson, et al., 1995. Electrophysiological effects of $\alpha_2$–adrenergic stimulation in canine cardiac Purkinje fibers, Am. J. Physiol. 268: H2024–H2035.

Martins, J., 1995. Purkinje involvement at focal origin of ischemic ventricular tachycardia. J. Invest. Med. 43: 431A (Abstract).

Castle, Neil A., 1992. Differential inhibition of potassium currents in rat ventricular myocytes by capsaicin. Cardiovasc. Res. 26: 1137–1144.

D'Alonzo, A.J., et al., 1995. In vitro effects of capsaicin: antiarrhythmic and antiischemic activity. Eur. J. Pharmacology 272: 269–278.

Franco–Cereceda, A., et al., 1988. Calcitonin gene–related peptide: release by capsaicin and prolongation of the action potential in the guinea–pig heart. Acta. Physiol. Scand. 132: 181–190.

Nakajima, T., et al., 1991. Effects of calcitonin gene–related peptide on membrane currents in mammalian cardiac myocytes. Eur. J. Physiology 419: 644–650.

Hess, T.A., et al., 1994. In vitro antiarrhythmic and antiischemic effects of capsaicin, a $K^+$ channel modulator. FASEB Abstracts (II) 3530.

Physician' Desk Reference, vol. 50, 1996. Dolorac™, p. 1054; Zostrix® and Zostrix®–HP, p. 1056.

*Primary Examiner*—Kevin E. Weddington
*Assistant Examiner*—M. Moezie
*Attorney, Agent, or Firm*—William J. McNichol, Jr.; R. Anthony Diehl

[57] ABSTRACT

The invention relates to the use of zucapsaicin (cis-8-methly-N-vanillly-6-nonenamide), the cis-isomer of capsaicin, to treat myocardial disorders, including the prevention, suppression or reversal of an abnormal cardiac rhythm, such as ventricular tachycardia. In vitro, zucapsaicin exhibits electrophysiologic properties distinct from capsaicin. In contrast to capsaicin, zucapsaicin significantly shortens the action potential duration at a dose of $10^{-5}$M and has no effect on the amplitude of Phase 1 of the action potential in normal Purkinje cells. Zucapsaicin also prevents the induction of ventricular tachycardia of focal Purkinje origin when given intravenously after coronary occlusion in a dog model of acute myocardial infarction.

1 Claim, 4 Drawing Sheets

METHOD FOR THE TREATMENT OF CARDIAC ARRHYTHMIAS AND SHORTENING OF ACTION POTENTIAL DURATION

BACKGROUND

Rapid treatment of cardiac arrhythmias, especially those occurring during ischemia, acute myocardial infarction or congestive heart failure, is vital to the patient. Arrhythmias, such as ventricular and atrial extrasystoles, and non-sustained ventricular tachycardia and bradycardia are commonly present from the onset of ischemia. These may lead to the most lethal of the arrhythmias, including sustained ventricular tachycardia and fibrillation which, if not treated promptly, lead to cardiopulmonary collapse and death. There is, therefore, a need for specific pharmacologically active compounds to treat myocardial disorders, including the prevention, suppression or reversal of abnormal cardiac rhythms, thereby preventing cardiac arrest, especially in ischemia, acute myocardial infarction or congestive heart failure.

Recently, in vitro studies have suggested that capsaicin (trans-8-methly-N-vanillly-6-nonenamide) may have potential antiarrhythmic and/or antiischemic activity. Capsaicin is a naturally occurring compound derived from plants of the Solanaceae family, commonly known as hot red peppers. The cis-isomer of capsaicin, zucapsaicin or civamide (cis-8-methly-N-vanillly-6-nonenamide), is not a naturally occurring compound, but is produced by means of chemical synthesis. Capsaicin has been used to study the neurophysiology and pharmacology of pain, and both capsaicin and zucapsaicin are now known to be effective pain relievers that are believed to act on peripheral sensory neurons to deplete and prevent reaccumulation of neuropeptides, such as substance P and calcitonin gene-related peptide (CGRP). Zucapsaicin is now believed to be even more potent as a depleter of neuropeptides from sensory nerves than is capsaicin.

In the nervous system, capsaicin-induced release of neuropeptides, such as substance P and calcitonin gene-related peptide (CGRP), is associated with certain electrophysiologic effects in the nerve cell membrane, including the opening of nonspecific cationic channels and changes in sodium, potassium and calcium ionic currents, that ultimately result in excitation of the neuron. Capsaicin also appears to affect the electro-physiologic properties of cells other than neurons. In vitro studies of the effect of capsaicin on normal, isolated rat ventricular myocytes have shown that $10^{-5}$M capsaicin causes prolongation of the action potential duration associated with inhibition of potassium ion channel conductances in the membrane, specifically the transient outward ($I_{to}$), delayed rectifier ($I_K$) and inward rectifier ($I_{K1}$) currents. (Castle, N., 1992, Cardiovasc. Res. 26:1137). This pharmacologic activity may account for the observation that when isolated, perfused rat and guinea pig hearts with experimentally-produced regional ischemia were treated with capsaicin, the incidence of ischemic ventricular tachycardia and/or ischemic ventricular fibrillation was significantly reduced. (D'Alonzo, A. J. et al. 1995, Eur. J. Pharmacology 272:269). The heart is innervated by noncholinergic, non-adrenergic sensory neurons which contain substance P and CGRP. Intravenous injection of capsaicin in animals has been shown to produce neural stimulation and release of CGRP which is known to be a potent coronary vasodilator. The cardiostimulatory actions of capsaicin (positive chronotropic and inotropic effects) are also thought to be due, in part, to CGRP release from sensory nerves within the heart in some animal species. (Franco-Cereceda, A., et al. 1988, Acta Physiol. Scand. 132:181). In summary, the effects of capsaicin at the level of the myocardium appear to be a complex mixture of direct actions on cardiac myocytes, as well as effects mediated by sensory nerve stimulation.

Although the in vitro studies suggest that capsaicin may be a potential antiarrhythmic compound, there is no evidence that capsaicin will prevent, suppress or reverse cardiac arrhythmias in vivo, or will do so in doses that are physiologically achievable and tolerable. Because zucapsaicin, the cis-isomer of capsaicin, is believed to be even more potent than capsaicin in neuropeptide depletion from peripheral sensory neurons, there is a need for evaluation of the electrophysiologic effects of zucapsaicin in the myocardium, especially in Purkinje fibers which conduct electrical impulses responsible for coordinated ventricular contraction. There is a further need for evaluation of the potential use of zucapsaicin to treat myocardial disorders, and to prevent, suppress or reverse heart arrhythmias, particularly in ischemia, acute myocardial infarction and congestive heart failure.

SUMMARY OF THE INVENTION

In accordance with the present invention, zucapsaicin was evaluated in vitro as to potential electrophysiologic effects in normal Purkinje tissue from the dog. Further, zucapsaicin was evaluated for its potential antiarrhythmic effects in an in vivo model of acute myocardial ischemia in the dog.

Surprisingly, zucapsaicin was discovered to have in vitro electrophysiologic properties that are distinct from those of capsaicin. It was discovered that zucapsaicin significantly shortens the action potential duration in normal Purkinje cells at a concentration of $10^{-5}$M and does not prolong the action potential duration at any concentration evaluated; whereas, $10^{-6}$M capsaicin significantly prolongs the action potential duration in normal Purkinje cells. Shortening of the action potential duration may be associated with the impediment of calcium entry into cells and with potential in vivo antiarrhythmic effects. Further, in contrast to capsaicin, zucapsaicin exhibited no significant change in the amplitude of Phase 1 of the action potential, which usually reflects the potassium ionic current, $I_{to}$; whereas capsaicin showed a diminished $I_{to}$ voltage, which was reversed upon removal of the drug.

Zucapsaicin was also discovered to prevent the induction of ventricular tachycardia, in an in vivo dog model of acute myocardial infarction, when given intravenously at a dose of 50 µg/kg, 1.5 to 2.5 hours after coronary artery occlusion.

Accordingly, the present invention relates to a composition comprising an admixture of zucapsaicin (cis-8methly-N-vanillly-6-nonenamide), with a pharmaceutically acceptable vehicle, the zucapsaicin being present in an amount sufficient to alter an electrophysiologic property of the myocardium and, preferably, to prevent, suppress or reverse an abnormal cardiac rhythm and restore a normal cardiac rhythm in a patient to whom the composition is administered. The composition may be administered to the patient by any route, including oral, transdermal, intravenous, intradermal, subcutaneous, intramuscular and cerebrospinal administration, or combinations of these. The zucapsaicin in the composition may be present in the amount of between about 5 µg/kg and about 500 µg/kg body weight, preferably about 50 µg/kg body weight, in a pharmaceutically acceptable vehicle.

The invention further relates to a method of treating a myocardial disorder, including ischemia, acute myocardial infarction and congestive heart failure, with zucapsaicin in an effective amount to alter an electrophysiologic property of the myocardium and to prevent, suppress or reverse an abnormal cardiac rhythm. The invention also includes a method of treating the myocardium with an amount of zucapsaicin effective to alter an electrophysiologic property of the myocardium, including shortening of the action potential duration of myocardial cells, and to prevent, suppress or reverse an abnormal cardiac rhythm, including ventricular arrhythmias, such as ventricular tachycardia.

BRIEF DESCRIPTION OF THE DRAWINGS

The present invention can be better understood by reference to the drawings in which.

DETAILED DESCRIPTION OF THE INVENTION

Figure 1:
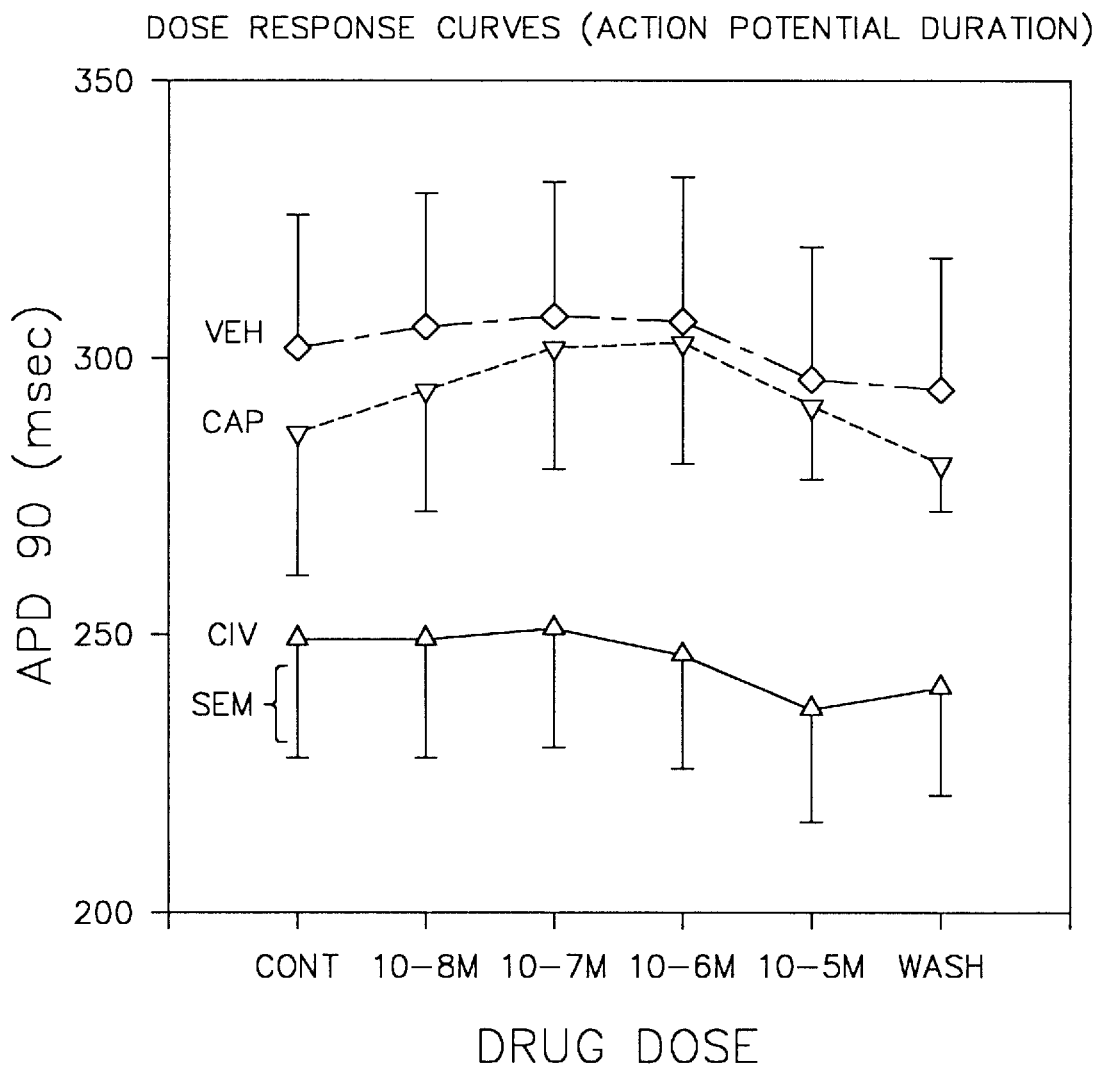
FIG. 1 illustrates dosage effects of zucapsaicin (CIV), capsaicin (CAP) and vehicle (VEH) on the action potential duration in isolated dog Purkinje fibers.

Zucapsaicin was evaluated in vitro as to potential electrophysiologic effects in normal Purkinje tissue from the dog. The details and results of the evaluation are provided in greater detail in the Examples below. In summary, the in vitro evaluation shows that zucapsaicin has electrophysiologic properties that, surprisingly, are distinct from those of capsaicin. In accordance with the invention, zucapsaicin significantly shortens the action potential duration in normal Purkinje cells at an in vitro concentration of $10^{-5}$M and does not prolong the action potential duration at any concentration evaluated; whereas, $10^{-6}$M capsaicin significantly prolongs the action potential duration in normal Purkinje cells. (This effect of capsaicin is similar to that shown in previous investigations, as described above.) Shortening of the action potential duration is believed to be associated with a blockade of the membrane calcium ionic current, $I_{Ca}$ or the ATP-dependent potassium current, $I_{KATP}$. Because damaged, ischemic cells are usually overloaded with calcium, these regions of myocardial ischemic tissue become prone to arrhythmias, especially ventricular tachycardia associated with delayed after-depolarizations (DAD). Therefore, compounds which impede calcium entry into the cell may prevent both DAD and ventricular tachycardia. The shortening of the action potential duration exhibited by zucapsaicin in vitro is reflective of a potential antiarrhythmic effect in vivo, in particular an inhibitory effect on ventricular tachycardia associated with DAD due to blocking of calcium entry into ischemic cells.

Further, in contrast to capsaicin, zucapsaicin exhibits no significant change in the amplitude of Phase 1 of the action potential, which usually reflects the potassium ionic current, $I_{to}$; whereas capsaicin shows a diminished $I_{to}$ voltage, which is reversed upon removal of the drug. (This effect of capsaicin is similar to that shown in previous investigations, as described above.) Therefore, the results show that surprising and significant electrophysiologic differences exist between effects of zucapsaicin and capsaicin on normal myocardial cells, such as Purkinje cells.

Zucapsaicin was also discovered to prevent the induction of ventricular tachycardia, in an in vivo dog model of acute myocardial infarction, when given intravenously at a dose of 50 µg/kg body weight, 1.5 to 2.5 hours after coronary occlusion.

In accordance with the invention, and as described more particularly in the Examples which follow, in vivo administration of a composition comprising an admixture of an effective amount of zucapsaicin with a pharmaceutically acceptable vehicle, alters an electrophysiologic property of the myocardium, including Purkinje cells and, preferably, prevents, suppresses or reverses abnormal cardiac rhythms, especially ventricular arrhythmias such as ventricular tachycardia. The zucapsaicin may be administered to the patient by any route, including oral, transdermal, intravenous, intradermal, subcutaneous, intramuscular and cerebrospinal administration, or combinations of these. The zucapsaicin may be administered in the amount of between about 5 µg/kg and about 500 µg/kg body weight, preferably about 50 µg/kg body weight, in a pharmaceutically acceptable vehicle. A 50 µg/kg intravenous dose of zucapsaicin is calculated to be approximately equivalent to an in vitro concentration of $10^{-5}$M or less, assuming a homogeneous distribution of the drug throughout the body. Zucapsaicin may be administered at any time during or after the onset of symptoms of ischemia, acute myocardial infarction or congestive heart failure. For example, in a model of acute myocardial infarction in a dog described in Example 2, zucapsaicin, given at between about 1.5 and 2.5 hours after coronary occlusion, was effective to prevent or suppress ventricular tachycardia for at least three hours after coronary occlusion. Preferably, administration of an effective dose of zucapsaicin restores a normal cardiac rhythm in the patient.

Any pharmaceutically acceptable vehicle may be utilized in the composition. For example, zucapsaicin in a suitable vehicle may be an appropriate dilution of a stock solution (VEH-X) comprising (w/w) 0.3% zucapsaicin, 1.166% dehydrated ethanol, 0.5% sodium chloride, 0.336% potassium phosphate, 8% polysorbate 20, 0.1% disodium ethlyenediaminetetracetate (EDTA), 0.0734% disodium phosphate, 0.02% benzalkonium chloride 50%, 0.0116% butlyated hydroxytoluene (BHT) and 89.493% water.

Turning now to the drawing figures, examples will be utilized to describe the invention.

EXAMPLE 1

To study the electrophysiologic properties of zucapsaicin, dose response curves were performed in isolated Purkinje fibers from the dog, utilizing standard intracellular microelectrode techniques. Measurements were made of the action potential duration (reflective of ionic currents, including calcium current, $I_{Ca}$), action potential amplitude (an index of sodium current, $I_{Na}$), and resting membrane potential (an index of potassium current, $I_{K1}$.

To isolate Purkinje fibers, anesthetized dogs underwent thoracotomy and rapid removal of the still beating heart. The heart was placed in a cold, oxygenated, electrolyte buffer. Purkinje fibers connecting muscle trabeculae were visually observed and were removed by a small scissors while the tissue was kept under the buffer. The free-running fibers were pinned to a tissue bath and superfused with buffer. After stabilization, the fibers were paced at a rate of 100 beats per minute and control electrophysiologic readings were taken. Incremental concentrations of zucapsaicin or capsaicin in a suitable dilution of vehicle (VEH-X), or vehicle alone, were then added to the isolated Purkinje fibers in the constant buffer superfusion. After an equilibration period at each concentration level, electrophysiologic readings were made. Following exposure to the highest concentration, the preparations were washed with buffer and electrophysiologic readings were again recorded to determine whether the effects of the intervention were reversible.

Measurements of action potential duration were made at the 90% repolarization level after the plateau region of the action potential (APD 90), utilizing standard intracellular recording techniques with electrodes filled with 3mM KCl and having a measured tip resistance of 12–45 ohms. As illustrated in FIG. 1, the vehicle (VEH) alone did not statistically (± standard error of the mean, SEM) alter the action potential duration of normal Purkinje fibers. As expected, capsaicin (CAP), the trans-isomer, significantly prolonged the action potential duration by about 20 milliseconds at a dose of $10^{-6}$M (p<0.05). In contrast, zucapsaicin or civamide (CIV), the cis-isomer, significantly shortened the action potential duration at a dose of $10^{-5}$M (p<0.05) and did not prolong the action potential duration at any dose utilized. Similar results were achieved when the action potential duration was measured at the 50% repolarization level (APD 50) (not shown).

Further standard electrophysiologic studies showed that neither zucapsaicin nor capsaicin at doses ranging from $10^{-8}$M to $10^{-5}$M had an effect on resting membrane potential ($I_{K1}$) or action potential amplitude ($I_{Na}$) in normal Purkinje fibers. However, capsaicin did show an expected diminished amplitude of Phase 1 of the action potential (reflective of the potassium current, $I_{to}$), which was reversed when the drug was washed from the cell preparation. In contrast, zucapsaicin did not alter the amplitude of Phase 1 of the action potential.

The results of the above studies show that surprising and significant electrophysiologic differences exist between the effects of the trans-isomer capsaicin and the cis-isomer zucapsaicin in normal Purkinje fibers. Zucapsaicin does not show any effect on potassium ionic currents, but capsaicin inhibits potassium ionic currents, particularly $I_{to}$. Zucapsaicin shows statistically significant shortening of the action potential duration at a dose of $10^{-5}$M which is physiologically achievable in vivo; whereas capsaicin at $10^{-6}$M lengthens the action potential duration.

EXAMPLE 2

In order to investigate the antiarrhythmic potential of zucapsaicin in vivo, studies were performed using 13 dogs undergoing induced acute myocardial infarction. Coronary artery occlusion was produced in the anaesthetized dogs by tying off the anterior descending coronary artery. Coronary occlusion was maintained for one hour in order to allow a stable ischemic zone to develop.

Prior to occluding the artery, 20 multipolar plunge needle electrodes were placed in the ischemic risk zone to record bipolar electrograms through the left ventricular wall of the myocardium. Three-dimensional maps of induced ventricular tachycardia were constructed from multiplexed signals for up to 14 seconds of data. The signals were digitized at 3 kHz and filtered from 3 to 1300 Hz, allowing recording of Purkinje activity on endocardial electrograms which recorded Purkinje activity underlying the area of myocardial infarction.

After stabilization of the ischemic zone, ventricular tachycardia was induced by as many as five early extrastimuli, which were programmed after a series of eight regular stimuli at a heart rate of 200 beats per minute. The ventricular tachycardia produced by this method is thought to be due either to "reentry" mechanisms or to delayed afterdepolarizations (DAD). Reentry is believed to be a source of abnormal cardiac rhythms, distinct from DAD, and is also found in ischemia. The ventricular tachycardia was monomorphic with a cycle length varying from 110 to 150 milliseconds, and originated from a focus in the endocardium.

After ventricular tachycardia was induced two separate times to show reproducibility, the test dogs were given 50 μg/kg body weight of zucapsaicin in a vehicle (a suitable dilution of the stock solution VEH-X) intravenously at between about 1.5 and 2.5 hours after the coronary occlusion. Attempts to induce ventricular tachycardia were repeated. In control dogs not given the drug, ventricular tachycardia induction was reproducible for at least three hours after occlusion. However, in zucapsaicin-treated dogs, ventricular tachycardia with a focal Purkinje origin (n=6) were not inducible again for at least three hours after occlusion. Therefore, zucapsaicin prevented or suppressed the induction of ventricular tachycardia in ischemic myocardium when focal Purkinje tissue was the origin of ventricular tachycardia. The effect of zucapsaicin on induction of epicardial reentrant ventricular tachycardia was also studied. It was found that epicardial reentrant ventricular tachycardia was also prevented by zucapsaicin but required a higher dose (about 200 μg/kg).

Figure 2:
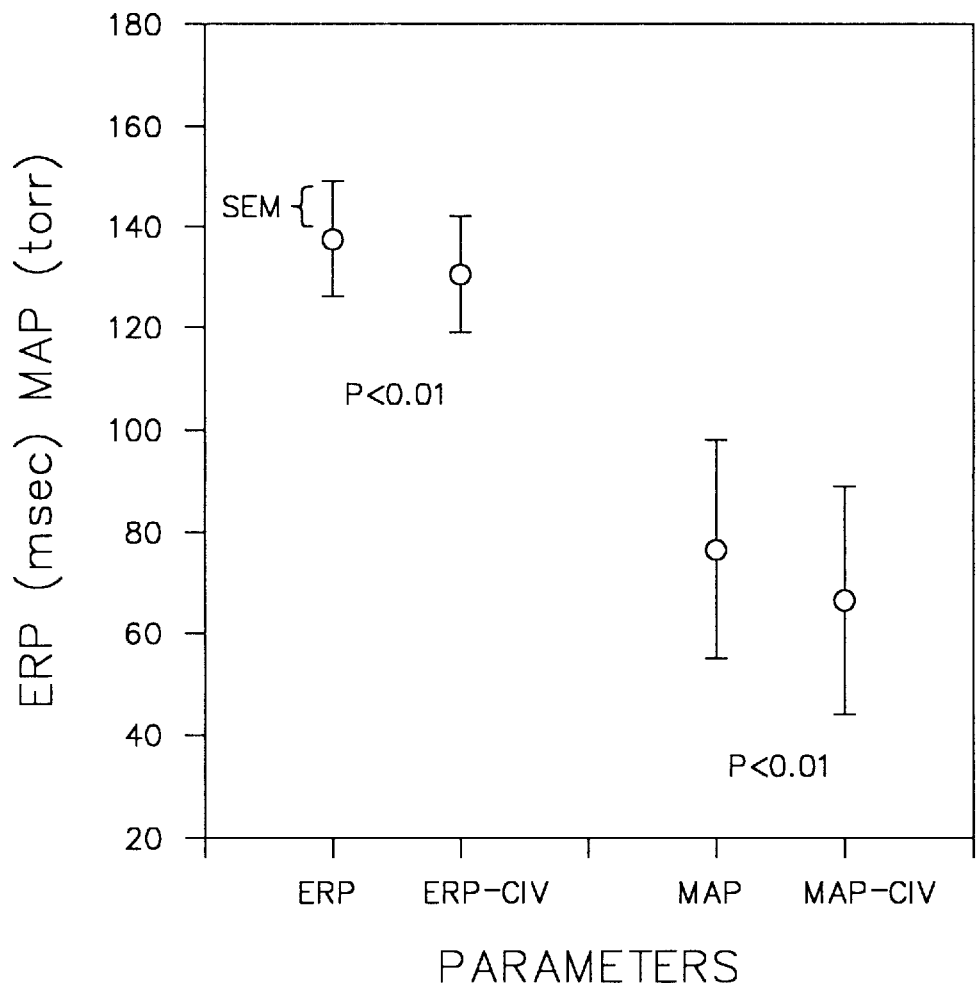
FIG. 2 illustrates the effects of 50 µg/kg intravenous zucapsaicin (Civamide, CIV) on the refractory period (ERP) in normal myocardium, and the mean arterial pressure (MAP).

As illustrated in FIG. 2, treatment with intravenous zucapsaicin (CIV) at 50 μg/kg body weight also produced shortening of the refractory period (ERP) in normal myocardium from 138±3 to 132±4 milliseconds (p<0.01), consistent with the shortening of the action potential duration demonstrated by zucapsaicin in vitro (see EXAMPLE 1). Zucapsaicin also decreased mean arterial pressure (MAP) from 76±7 to 66±7 mmHg (p<0.05).

Figure 3:
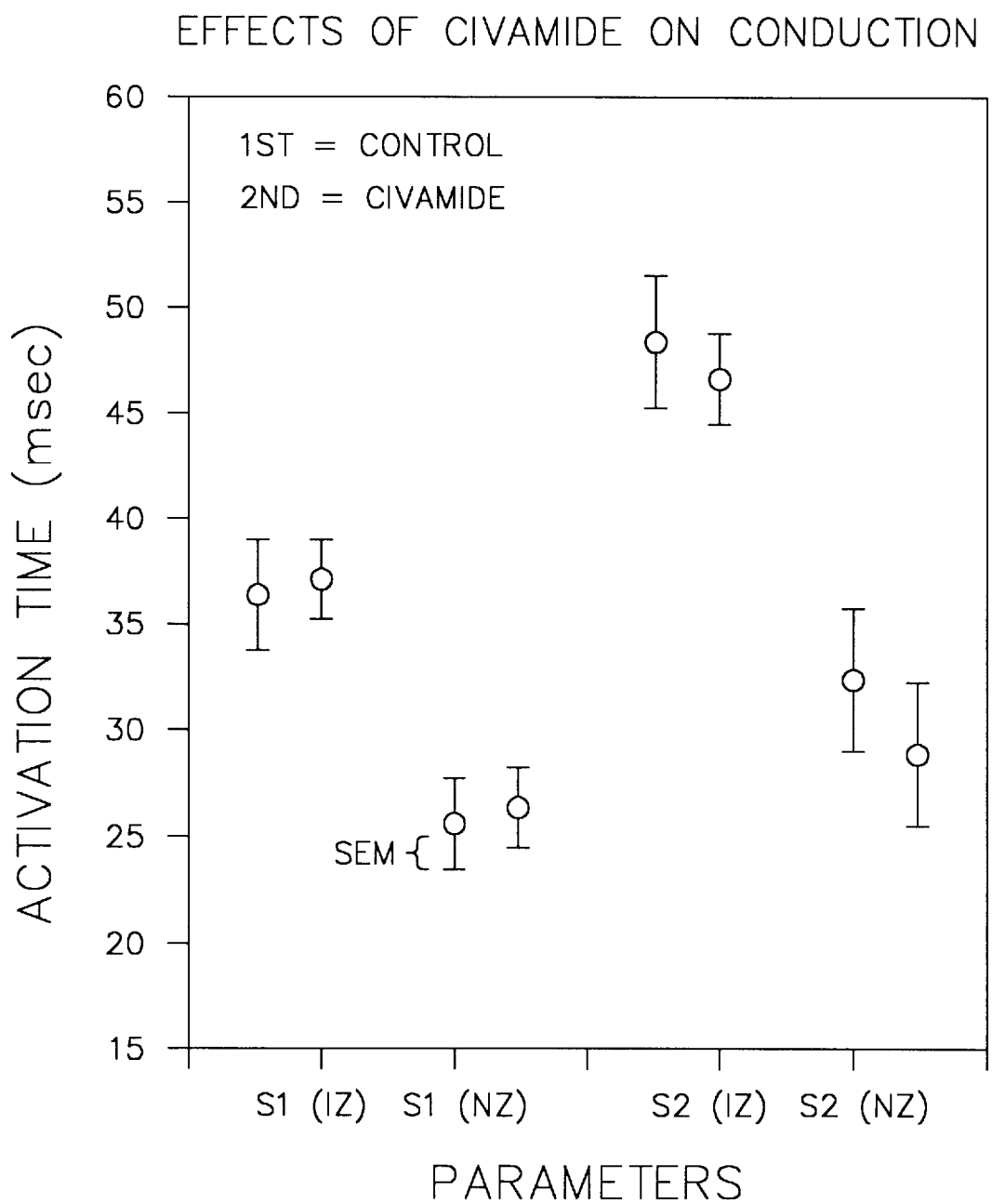
FIG. 3 illustrates the effects of 50 µg/kg intravenous zucapsaicin (Civamide) on activation times in a normal zone (NZ) and ischemic zone (IZ) in dog myocardium after coronary artery occlusion.

Further, as illustrated in FIG. 3, zucapsaicin treatment did not significantly alter activation times of drive (S1) or premature (S2) stimuli in normal (NZ) or ischemic (IZ) zones. These results are consistent with the absence of significant effects by zucapsaicin at this dose on $I_{Na}$, in vitro. In dogs which did not have inducible ventricular tachycardia after coronary occlusion (n=3), treatment with zucapsaicin intravenously up to 500 μg/kg body weight did not provoke ventricular tachycardia.

Figure 4:
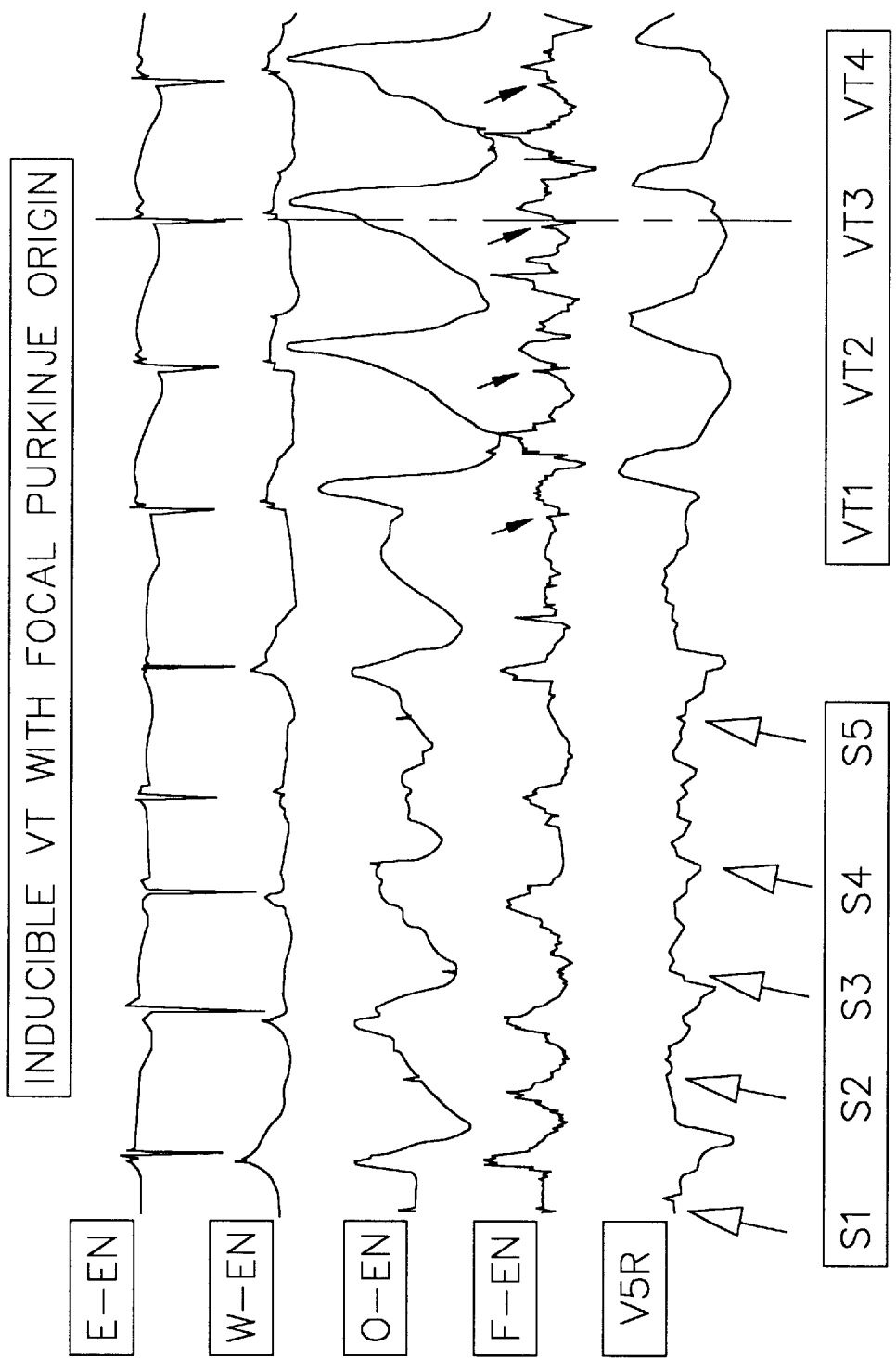
FIG. 4 shows endocardial electrograms and surface ECG V5R after coronary artery occlusion in a dog, illustrating inducible ventricular tachycardia (VT) with focal Purkinje origin (closed arrows) preceding each QRS (VT3 marked by vertical line).

As shown in FIG. 4, in one animal with endocardial focal ventricular tachycardia induced with four extra stimuli S2–S5 (open arrows on V5R), Purkinje activity was recorded (filled arrows on F-EN) prior to the QRS (V5R, vertical line) and prior to any endocardial (EN, E: east, W: west, O: overlying) or epicardial activity occurring within the risk zone. These and other experimental data by applicants suggest that Purkinje tissue underlying an area of myocardial ischemia may be the source of ventricular tachycardia. (Martins, J., 1995, J. Invest. Med. 43:431A). Since Purkinje cells are more likely to show DAD than myocytes, the data of FIG. 4 are consistent with DAD-mediated ventricular tachycardia originating in Purkinje cells. Therefore, in this model, zucapsaicin is also effective to prevent or suppress the induction of ventricular tachycardia originating in Purkinje tissue.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A method of preventing, suppressing or reversing an abnormal cardiac rhythm in a patient having a myocardial disorder, comprising:

administering to a patient having a disorder of the myocardium a composition comprising an admixture of cis-8-methly-N-vanillly-6-nonenamide in a pharmaceutically acceptable vehicle, said cis-8-methly-N-vanillly-6-nonenamide being administered to the patient in an amount sufficient to alter an electrophysiologic property of the myocardium, to prevent, suppress or reverse an abnormal cardiac rhythm, and to shorten the action potential duration.

* * * * *